(12) United States Patent
Otomo et al.

(10) Patent No.: US 8,465,924 B2
(45) Date of Patent: Jun. 18, 2013

(54) TREATMENT SOLUTION FOR PREPARING SAMPLE SOLUTION FOR NUCLEIC ACID AMPLIFICATION REACTION AND METHOD FOR DETECTING NUCLEIC ACID BY USING TREATMENT SOLUTION

(75) Inventors: Yasuhiro Otomo, Kobe (JP); Kazuhiko Takeda, Fujidera (JP); Shigeki Abe, Kobe (JP); Kazuki Nakabayashi, Kobe (JP)

(73) Assignee: Sysmex Corporation, Hyogo (JP)

( * ) Notice: Subject to any disclaimer, the term of this patent is extended or adjusted under 35 U.S.C. 154(b) by 56 days.

(21) Appl. No.: 11/294,545

(22) Filed: Dec. 6, 2005

(65) Prior Publication Data

US 2006/0121515 A1 Jun. 8, 2006

(30) Foreign Application Priority Data

Dec. 7, 2004 (JP) ................. 2004-353849

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
None
See application file for complete search history.

(56) References Cited

U.S. PATENT DOCUMENTS

| 3,673,655 | A | 7/1972 | Eydieux |
| 7,384,739 | B2 * | 6/2008 | Kitabayashi et al. ............. 435/6 |
| 2005/0089857 | A1 | 4/2005 | Tada et al. |

FOREIGN PATENT DOCUMENTS

| WO | 94/02639 | 2/1994 |
| WO | WO 00/08136 A1 | 2/2000 |
| WO | WO 03 042383 A1 * | 5/2003 |
| WO | WO 2004/072270 A1 * | 8/2004 |

OTHER PUBLICATIONS

Alcock et al. (1999) J. Clin. Pathol.: Mol. Pathol. vol. 52: pp. 160-163.*
Qiagen Supplementary Protocol Sep. 2001 pp. 1-6.*
Chakrabarti & Schutt (2001) Gene vol. 274: pp. 293-298.*
Innis et al., editors, PCR Applications, Protocols for Functional Genomics, by Academic Press, San Diego, California, 1999, pp. 5 and 6.*
Alcock et al., A simple method for PCR based analyses of immunohistochemically stained, microdissected, formalin fixed, paraffin wax embedded material. Mol Path, 1999, 52: 160-163.*
Lemarchand et al, "*Optimization of Microbial DNA Extraction and Purification From Raw Wastewater Samples From Dowstream Pathogen Detection by Microarrays*", vol. 63, No. 2, Nov. 2005, pp. 115-126, XP005113146.
Jung et al, "*Dimethyl Sulfoxide as Additive in Ready-to-Use Reaction Mixtures for Real-Time Polymerase Chain Reaction Analysis with SYBR Green I Dye*", vol. 289, 2001, pp. 292-295, XP002366126.

* cited by examiner

*Primary Examiner* — Kenneth R. Horlick
*Assistant Examiner* — David Thomas
(74) *Attorney, Agent, or Firm* — Sughrue Mion, PLLC

(57) ABSTRACT

A treatment solution for preparing a sample solution for nucleic acid amplification reaction is described. The treatment solution comprises dimethyl sulfoxide and aqueous solvent. The sample solution prepared by treating a biological sample with the treatment solution is used in the amplification reaction of a nucleic acid, whereby the nucleic acid can be efficiently recovered from a biological sample, and the influence of an inhibitor during nucleic acid amplification can be effectively reduced.

11 Claims, 4 Drawing Sheets

SEQUENCE LISTING

<160> NUMBER OF SEQ ID NOS: 15

<210> SEQ ID NO 1
<211> LENGTH: 39
<212> TYPE: DNA
<213> ORGANISM: Artificial
<220> FEATURE:
<223> OTHER INFORMATION: Designed DNA based on Beta-actin gene

<400> SEQUENCE: 1
tgaaggtagt tcgtggatg cctgaggcac tcttccagc                39

<210> SEQ ID NO 2
<211> LENGTH: 38
<212> TYPE: DNA
<213> ORGANISM: Artificial
<220> FEATURE:
<223> OTHER INFORMATION: Designed DNA based on Beta-actin gene

<400> SEQUENCE: 2
tgaagtgtga cgtggacatc cagggtacat ggtggtgc                38

<210> SEQ ID NO 3
<211> LENGTH: 17
<212> TYPE: DNA
<213> ORGANISM: Artificial
<220> FEATURE:
<223> OTHER INFORMATION: Designed DNA based on Beta-actin gene

<400> SEQUENCE: 3
tggcaatgag cggttcc                                        17

<210> SEQ ID NO 4
<211> LENGTH: 18
<212> TYPE: DNA
<213> ORGANISM: Artificial
<220> FEATURE:
<223> OTHER INFORMATION: Designed DNA based on Beta-actin gene

<400> SEQUENCE: 4
tccttctgca tcctgtcg                                       18

<210> SEQ ID NO 5
<211> LENGTH: 16
<212> TYPE: DNA
<213> ORGANISM: Artificial
<220> FEATURE:
<223> OTHER INFORMATION: Designed DNA based on Beta-actin gene

<400> SEQUENCE: 5
acaggactcc atgccc                                         16

<210> SEQ ID NO 6
<211> LENGTH: 18
<212> TYPE: DNA
<213> ORGANISM: Artificial
<220> FEATURE:
<223> OTHER INFORMATION: Designed DNA based on Beta-actin gene

<400> SEQUENCE: 6
tgtacgccaa cacagtgc                                       18

<210> SEQ ID NO 7
<211> LENGTH: 38
<212> TYPE: DNA

```
<213> ORGANISM: Artificial
<220> FEATURE:
<223> OTHER INFORMATION: Designed DNA based on GAPDH gene

<400> SEQUENCE: 7
cagaaggggc ggagatgatg caccaccatg gagaaggc                            38

<210> SEQ ID NO 8
<211> LENGTH: 38
<212> TYPE: DNA
<213> ORGANISM: Artificial
<220> FEATURE:
<223> OTHER INFORMATION: Designed DNA based on GAPDH gene

<400> SEQUENCE: 8
tgatgggtgt gaaccacgag gcaggatgca ttgctgac                            38

<210> SEQ ID NO 9
<211> LENGTH: 18
<212> TYPE: DNA
<213> ORGANISM: Artificial
<220> FEATURE:
<223> OTHER INFORMATION: Designed DNA based on GAPDH gene

<400> SEQUENCE: 9
tgtcgtggag tctactgg                                                  18

<210> SEQ ID NO 10
<211> LENGTH: 17
<212> TYPE: DNA
<213> ORGANISM: Artificial
<220> FEATURE:
<223> OTHER INFORMATION: Designed DNA based on GAPDH gene

<400> SEQUENCE: 10
gggggctaag cagttgg                                                   17

<210> SEQ ID NO 11
<211> LENGTH: 19
<212> TYPE: DNA
<213> ORGANISM: Artificial
<220> FEATURE:
<223> OTHER INFORMATION: Designed DNA based on GAPDH gene

<400> SEQUENCE: 11
tggctccacc cttcaagtg                                                 19

<210> SEQ ID NO 12
<211> LENGTH: 21
<212> TYPE: DNA
<213> ORGANISM: Artificial
<220> FEATURE:
<223> OTHER INFORMATION: Designed DNA based on GAPDH gene

<400> SEQUENCE: 12
aatatgacaa ctcactcaag a                                              21

<210> SEQ ID NO 13
<211> LENGTH: 20
<212> TYPE: DNA
<213> ORGANISM: Artificial
<220> FEATURE:
<223> OTHER INFORMATION: Designed DNA based on CK19 gene

<400> SEQUENCE: 13
cagatcgaag gcctgaagga                                                20
```

```
<210> SEQ ID NO 14
<211> LENGTH: 19
<212> TYPE: DNA
<213> ORGANISM: Artificial
<220> FEATURE:
<223> OTHER INFORMATION: Designed DNA based on CK19 gene

<400> SEQUENCE: 14
cttggcccct cagcgtact                                              19

<210> SEQ ID NO 15
<211> LENGTH: 30
<212> TYPE: DNA
<213> ORGANISM: Artificial
<220> FEATURE:
<223> OTHER INFORMATION: Designed DNA based on CK19 gene

<400> SEQUENCE: 15
gcctacctga agaagaacca tgaggaggaa                                  30
```

TREATMENT SOLUTION FOR PREPARING SAMPLE SOLUTION FOR NUCLEIC ACID AMPLIFICATION REACTION AND METHOD FOR DETECTING NUCLEIC ACID BY USING TREATMENT SOLUTION

TECHNICAL FIELD

The present invention relates to a treatment solution for preparing a sample solution used in amplification reaction of a target nucleic acid. The present invention also relates to a method for preparing a sample solution used in amplification reaction of a nucleic acid, which comprises using the treatment solution. Further, the present invention relates to a method for detecting a target nucleic acid, which comprises using the treatment solution. In addition, the present invention relates to a kit for amplifying a target nucleic acid, which comprises the treatment solution.

BACKGROUND

Polymerase chain reaction (PCR) is a method of amplifying a nucleic acid wherein a target DNA fragment can be exponentially amplified by repeatedly carrying out dissociation of a DNA chain into a single strand, subsequent bonding, to the DNA strand, of a primer corresponding to a specific region in the strand, and DNA synthesis reaction with a DNA polymerase. In addition to the PCR method, there are nucleic acid amplification methods such as RT-PCR (reverse transcriptase-polymerase chain reaction), NASBA (nucleic acid sequence based amplification), LAMP (loop mediated isothermal amplification of DNA), TMA (transcription mediated amplification method) and 3SR (self-sustained sequence replication).

The amplification reaction of a nucleic acid in the nucleic acid amplification methods mentioned above is susceptible to the influence of a substance inhibiting the nucleic acid amplification reaction, such as a protein (hereinafter, referred to an inhibitor) contained in a biological sample, and the nucleic acid amplification reaction is inhibited by the inhibitor. Accordingly, the operation of extracting or purifying a nucleic acid component such as DNA or RNA from a biological sample is necessary prior to detection of a nucleic acid by the nucleic acid amplification method. However, the operation of extracting or purifying a nucleic acid component is troublesome and time-consuming. As methods capable of amplifying a target nucleic acid without conducting the operation of extracting or purifying a nucleic acid component, methods described in US Patent Application Laid-Open No. 2005/0089857 or International Laid-Open No. 00/08136 are known.

US Patent Application Laid-Open No. 2005/0089857 supra describes a method of amplifying a target nucleic acid, which comprises treating a biological sample with a solution containing a salt interacting with an inhibitor in order to reduce the influence of the inhibitor.

International Laid-Open No. 00/08136 supra describes a method of amplifying a nucleic acid from a microorganism present in a sample such as feces, which comprises washing the sample with an organic solvent to remove an inhibitor. Specifically, when the sample is feces, the feces are suspended in a suitable buffer solution, and the resulting suspension is centrifuged to remove large solids, and its supernatant is collected. The obtained supernatant is centrifuged, and the resulting supernatant is discarded, and the residual precipitates are washed by adding an organic solvent and centrifuging the precipitates, and microorganisms are recovered as the precipitates and used as a sample for nucleic acid amplification. International Laid-Open No. 00/08136 supra describes that hydrophilic organic solvents such as ethanol, methanol, 2-propanol, propanone (acetone), ethane nitrile (acetonitrile) and dimethyl sulfoxide (DMSO) or amphiphatic organic solvents such as butanol, 2-butanol and ethyl acetate can be used as the organic solvent. International Laid-Open No. 00/08136 also describes that the sample may be tissues collected surgically from the living body, a solid sample such as a tissue is desirably homogenized to facilitate washing, and a nucleic acid as the subject of amplification is not particularly limited to a gene of a pathogenic microorganism or a gene derived from the living body.

In the method in International Laid-Open No. 00/08136, however, a tissue derived from a living body is used as the sample, and when a nucleic acid derived from the tissue but not a nucleic acid in a microorganism present in the tissue is to be amplified, there arises a problem that when the homogenized tissue is washed with the above-mentioned organic solvent, the objective nucleic acid is removed together with an inhibitor, thus reducing the nucleic acid which can be recovered.

SUMMARY

The scope of the present invention is defined solely by the appended claims, and is not affected to any degree by the statements within this summary.

A first aspect of the present invention relates to a treatment solution for preparing a sample solution for nucleic acid amplification reaction by treating a biological sample, comprising dimethyl sulfoxide and aqueous solvent, wherein the sample solution contains nucleic acid which is transferred from the biological sample.

A second aspect of the present invention relates to a method for preparing a sample solution for nucleic acid amplification reaction, comprising the steps of: providing a dimethyl sulfoxide-containing treatment solution; and treating a biological sample with the treatment solution, so as to obtain the sample solution containing nucleic acid which is transferred from the biological sample.

A third aspect of the present invention relates to a method for detecting a target nucleic acid, comprising the steps of: preparing a sample solution for nucleic acid amplification reaction by treating a biological sample with a dimethyl sulfoxide-containing treatment solution, the sample solution containing nucleic acid which is transferred from the biological sample; amplifying the target nucleic acid contained in the sample solution; and detecting the amplified target nucleic acid.

A forth aspect of the present invention relates to a reagent kit for amplifying a target nucleic acid, comprising: a first reagent for treating a biological sample, comprising a dimethyl sulfoxide-containing treatment solution; and a second reagent for nucleic acid amplification reaction, comprising deoxyribonucleotide triphosphates, a DNA polymerase and a primer which is complementary to the target nucleic acid.

DESCRIPTION OF THE PREFERRED EMBODIMENTS

Figure 1:
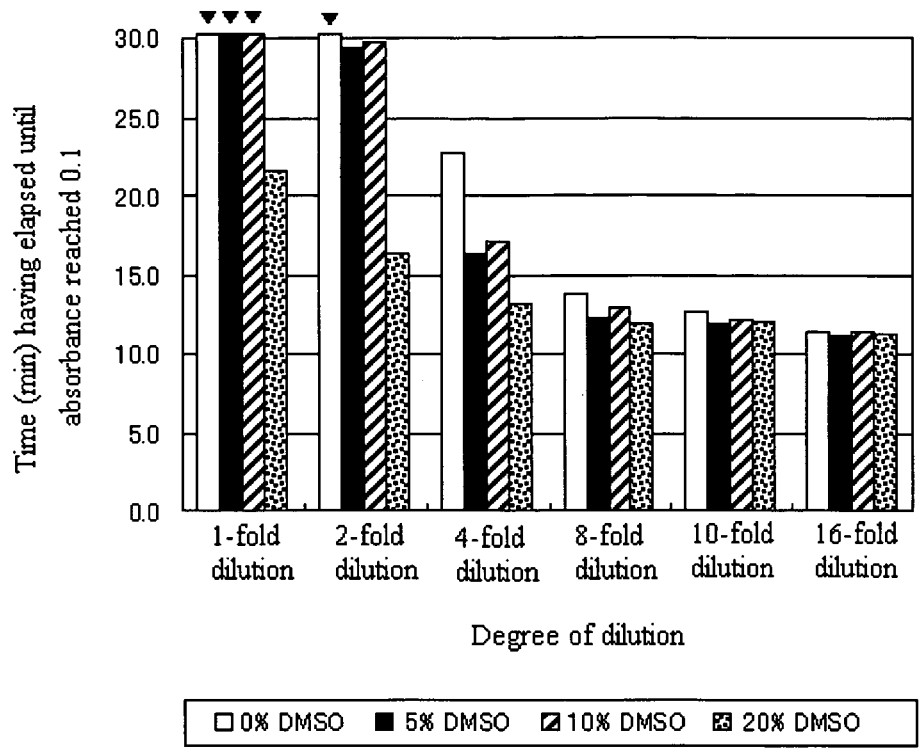
FIG. 1 is a graph showing the results in Example 1.
Figure 2:
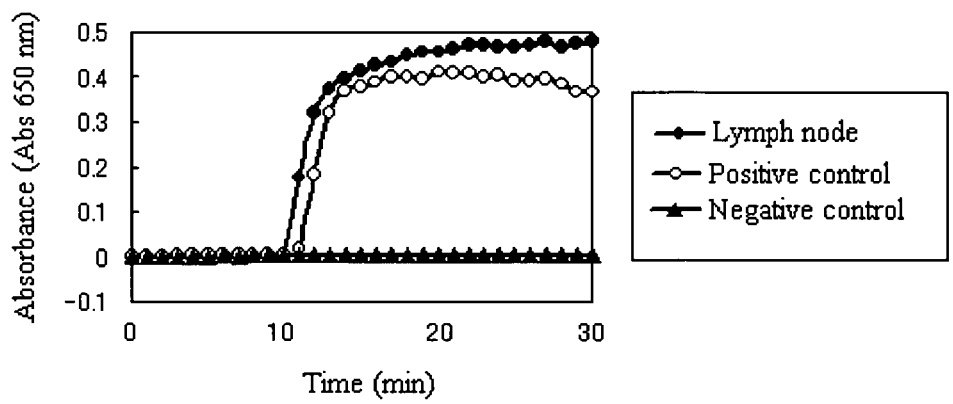
FIG. 2 is a graph showing the results in Example 2 wherein the lymph node was used as a biological sample.
Figure 3:
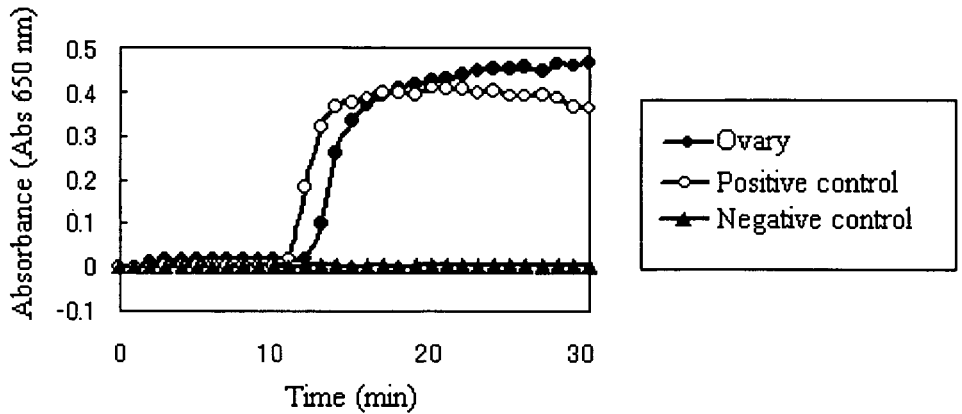
FIG. 3 is a graph showing the results in Example 2 wherein the ovary was used as a biological sample.
Figure 4:
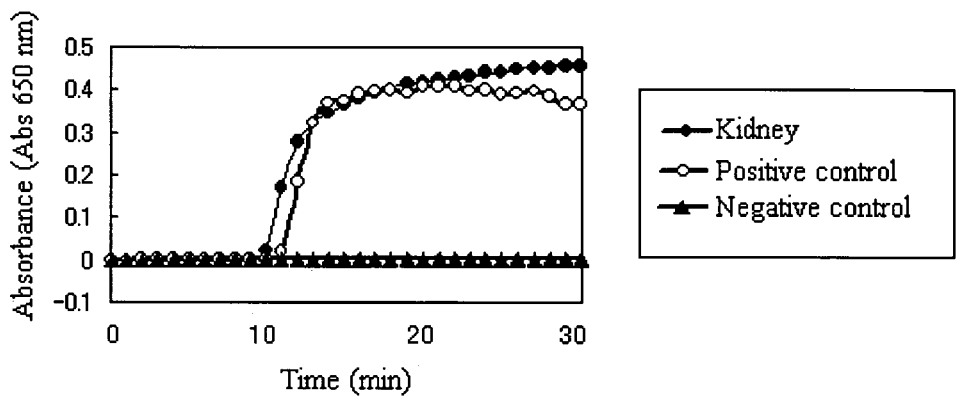
FIG. 4 is a graph showing the results in Example 2 wherein the kidney was used as a biological sample.
Figure 5:
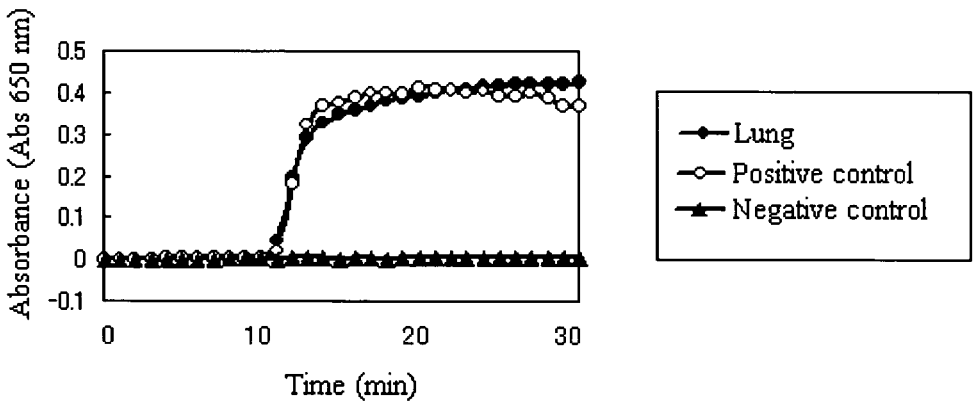
FIG. 5 is a graph showing the results in Example 2 wherein the lung was used as a biological sample.
Figure 6:
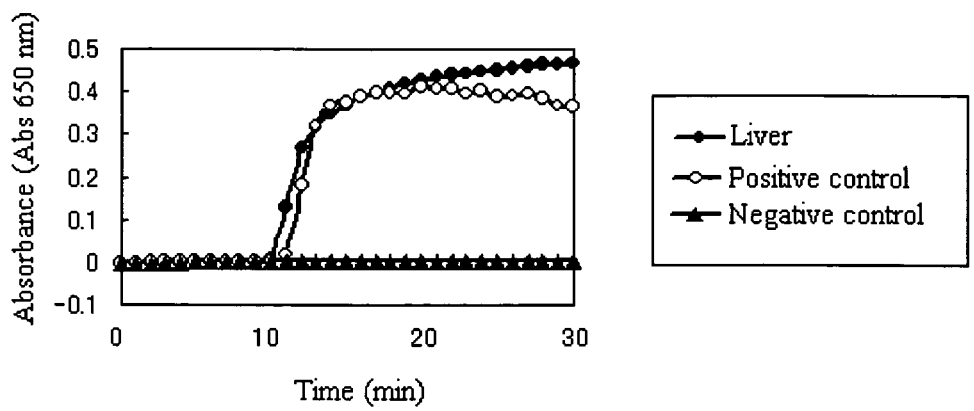
FIG. 6 is a graph showing the results in Example 2 wherein the liver was used as a biological sample.
Figure 7:
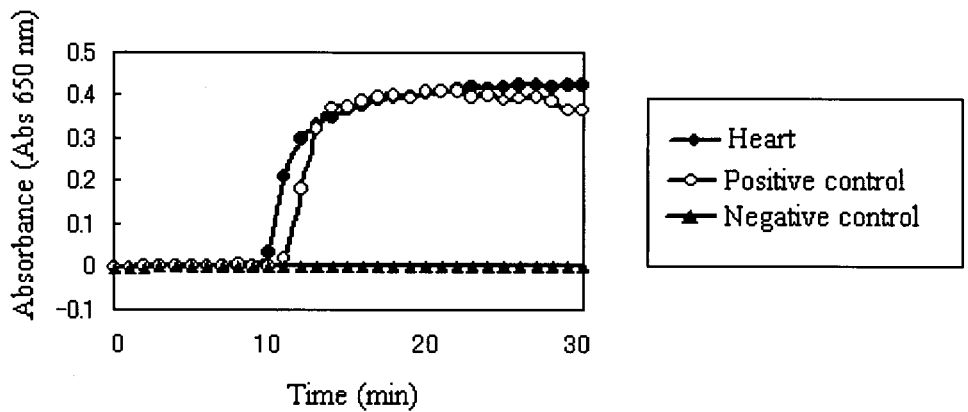
FIG. 7 is a graph showing the results in Example 2 wherein the heart was used as a biological sample.
Figure 8:
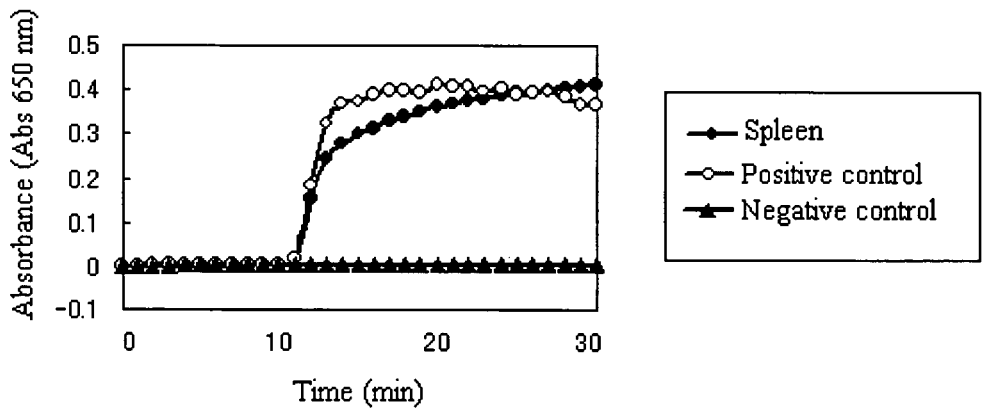
FIG. 8 is a graph showing the results in Example 2 wherein the spleen was used as a biological sample.
Figure 9:
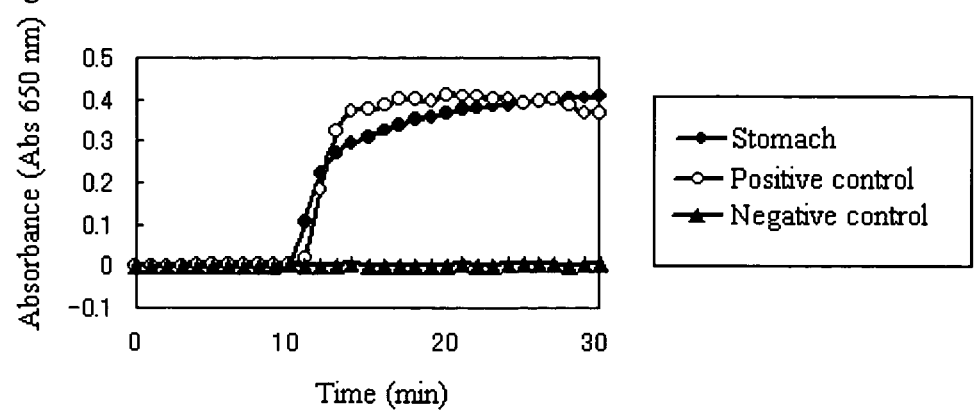
FIG. 9 is a graph showing the results in Example 2 wherein the stomach was used as a biological sample.
Figure 10:
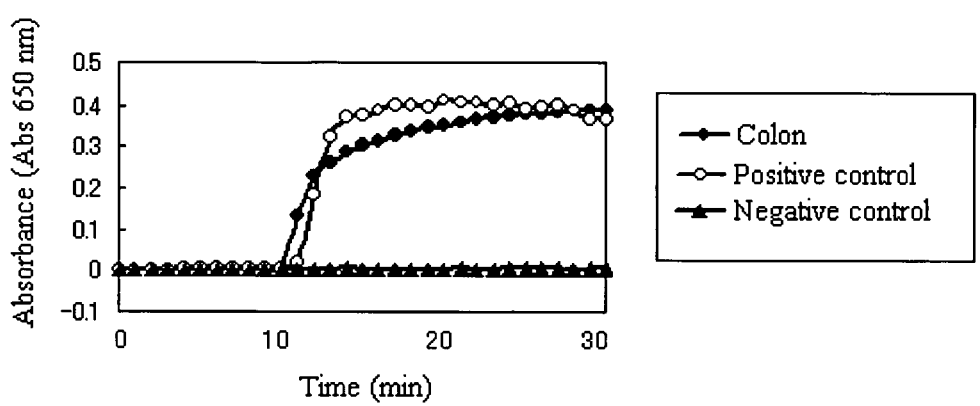
FIG. 10 is a graph showing the results in Example 2 wherein the colon was used as a biological sample.

The treatment solution for preparing a sample solution for nucleic acid amplification reaction contains dimethyl sulfoxide (DMSO) in order to reduce the influence of an inhibitor. A sample solution prepared by treating a biological sample with the treatment solution to transfer a nucleic acid contained in the biological sample to the treatment solution is used in the amplification reaction of a nucleic acid, whereby the nucleic acid can be efficiently recovered even if it is derived from a tissue, and the influence of an inhibitor during nucleic acid amplification can be effectively reduced.

The treatment solution is a solution obtained by dissolving dimethyl sulfoxide (DMSO) in aqueous solvent. The concentration of DMSO in the treatment solution is preferably 1 to 50% (v/v), more preferably 5 to 30% (v/v), still more preferably 10 to 25% (v/v). The treatment solution containing DMSO at the concentration is used to treat a biological sample thereby preparing a sample solution for nucleic acid amplification, and the sample solution is used in amplification reaction of a nucleic acid, whereby a possible drop in enzyme activity in the nucleic acid amplification reaction can be reduced, and the influence of an inhibitor during nucleic acid amplification can be effectively reduced.

To prevent degradation of a nucleic acid contained in the sample solution, an acidic treatment solution which is less than pH7.0 is desirably used. The pH of the treatment solution is preferably 2.5 to 5.0, more preferably 3.0 to 4.0.

The aqueous solvent includes water and a buffer solution. For example, the buffer solution which allows the pH of solution to be kept acidic can be used as aqueous solvent to prepare the acidic treatment solution.

The treatment solution further contains a surfactant in order to increase the amount of a nucleic acid contained in the sample solution for nucleic acid amplification reaction. The surfactant contained in the treatment solution is preferably a nonionic surfactant. Among various nonionic surfactants, a polyoxyethylene-based nonionic surfactant is preferable. The polyoxyethylene-based nonionic surfactant is particularly preferably a surfactant represented by the following general formula:

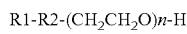

R1-R2-(CH$_2$CH$_2$O)$n$-H wherein R1 represents a C10 to C22 alkyl group, alkenyl group, alkynyl group or isooctyl group; R2 represents —O— or —(C$_6$H$_4$)—O—; and n is an integer of 8 to 120.

Preferable examples of the polyoxyethylene-based nonionic surfactant include polyoxyethylene lauryl ether, polyoxyethylene cetyl ether, polyoxyethylene oleyl ether, polyoxyethylene myristyl ether, polyoxyethylene stearyl ether, polyoxyethylene nonyl phenyl ether, and polyoxyethylene isooctyl phenyl ether. The concentration of the surfactant in the treatment solution is selected so as to be a preferable concentration depending on the type of the surfactant used. For example, the concentration of the nonionic surfactant in the treatment solution is preferably 0.1 to 6% (v/v), more preferably 1 to 5% (v/v). The treatment solution may also contain a defoaming agent together with the surfactant.

The biological sample is not particularly limited. For example, the biological sample include tissues such as lymph node or whole blood, plasma, serum, urine, saliva, body fluid and secretions collected from living bodies such as humans or animals. The biological sample also includes cultured tissues and cultured cells obtained by culturing tissues or cells collected from humans or animals. Further, the biological sample includes samples derived from non-animals such as plants and microorganisms.

The sample solution for nucleic acid amplification reaction is a solution obtained by mixing a biological sample with the treatment solution, and contains a nucleic acid serving as a template in nucleic acid amplification reaction. For use in the amplification reaction of the nucleic acid, the sample solution is mixed with reagents for nucleic acid amplification reaction. The reagents for nucleic acid amplification reaction include deoxyribonucleotide triphosphates, enzymes such as a DNA polymerase and RNA reverse transcriptase, at least one kind of primer which is complementary to the target nucleic acid, and a buffer solution giving preferable conditions to the enzyme reaction. Further, the reagents for nucleic acid amplification reaction can be combined with the treatment solution to constitute a reagent kit for amplifying a target nucleic acid. For example, when the reagent kit comprises a first reagent for treating a biological sample and a second reagent for nucleic acid amplification reaction, the first reagent comprises a dimethyl sulfoxide-containing treatment solution and the second reagent comprises deoxyribonucleotide triphosphates, enzymes such as a DNA polymerase and RNA reverse transcriptase and a primer which is complementary to the target nucleic acid. To constitute the second reagent, a first group reagent containing deoxyribonucleotide triphosphates and enzymes such as a DNA polymerase and RNA reverse transcriptase can be combined with a second group reagent containing a primer which is complementary to the target nucleic acid. Further, a first group reagent containing deoxyribonucleotide triphosphates and a primer which is complementary to the target nucleic acid can be combined with a second group reagent containing enzymes such as a DNA polymerase and RNA reverse transcriptase. Also, a first group reagent containing deoxyribonucleotide triphosphates can be combined with a second group reagent containing enzymes such as a DNA polymerase and RNA reverse transcriptase and a third group reagent containing a primer which is complementary to the target nucleic acid.

When the sample solution is prepared by mixing a biological sample with the treatment solution, cells containing a target nucleic acid are disrupted or lyzed to transfer the nucleic acid in the cells to the treatment solution. Particularly, when a solid sample such as a tissue is used as the biological sample, the sample solution is desirably rendered homogeneous with a homogenizer, a blender or the like in preparing the sample solution by mixing the biological sample with the treatment solution. To remove relatively large solid materials such as cell debris, the sample solution rendered homogenous may be subjected if necessary to treatment such as filtration and centrifugation in preparing the sample solution.

The target nucleic acid includes, but is not limited to, DNA and RNA derived from the living body, microbial DNA and RNA, and DNA and RNA derived from plants.

The inhibitor refers to a substance inhibiting the amplification reaction of a nucleic acid, and examples of the inhibitor include proteins, lipids and sugars contained in the biological sample. When the inhibitor is contained in the sample solution prepared from the biological sample, the amplification reaction of a nucleic acid is inhibited due to the influence of the inhibitor.

The influence of the inhibitor can be reduced by decreasing the concentration of the inhibitor in the sample solution. The method of decreasing the concentration of the inhibitor includes dilution of the sample solution. However, the concentration of the target nucleic acid in the sample solution is also decreased by dilution of the sample solution. Particularly, when the amount of a target nucleic acid in the biological sample is low, the concentration of the target nucleic acid in the sample solution is made very low upon dilution at high degree, resulting in problems such as necessity for a long time in nucleic acid amplification, a lower level of the amplified nucleic acid than the limit of detection, and failure to amplify the nucleic acid. Accordingly, the DMSO-containing treatment solution can be used to reduce the influence of an inhibitor contained in the sample solution, without diluting the sample solution at high degree. The optimum degree of dilution for amplifying a nucleic acid by effectively reducing the influence of an inhibitor varies depending on the amount and type of the biological sample used. Accordingly, when the sample solution is prepared from a biological sample by using the treatment solution, a suitable degree of dilution is selected desirably depending on the amount and type of the biological sample used. For dilution, the treatment solution can be used.

The sample solution prepared from a biological sample by using the treatment solution can be used in known methods for amplifying nucleic acids. Mention can be made of methods for amplifying nucleic acids, such as PCR (polymerase chain reaction), RT-PCR (reverse transcriptase-polymerase chain reaction), LAMP (loop mediated isothermal amplification of DNA), RT-LAMP (reverse transcriptase-loop mediated isothermal amplification of DNA), TMA (transcription mediated amplification method), NASBA (nucleic acid sequence-based amplification), 3SR (self-sustained sequence replication), SDA (standard displacement amplification) and ICAN (isothermal and chimeric primer-initiated amplification of nucleic acids). As one kind of nucleic acid amplification methods, mention can also be made of signal amplification methods such as RCA (rolling circle amplification), INVADER, CPT (cycling probe technology) and PALSAR (probe alternation link self-assembly reaction). In the signal amplification method, not the target nucleic acid itself but a specific nucleotide sequence complementary to the target nucleic acid is amplified. The nucleic acid amplification method is preferably PCR, RT-PCR, LAMP or RT-LAMP, particularly preferably LAMP or RT-LAMP from the viewpoint of rapidly amplifying the nucleic acid.

The method of detecting the amplified target nucleic acid is not particularly limited, and the target nucleic acid can be detected by methods known in the art. It is possible to employ, for example, agarose gel electrophoresis, a real-time detection method of detection with probes using a fluorescent label, and a method of detection by the turbidity of a byproduct generated upon DNA synthesis. If necessary, use can also be made of a method of detecting a target nucleic acid by confirming a nucleic acid cleavage pattern obtained by enzyme treatment, a method of detecting a target nucleic acid by determining its nucleotide sequence by sequence analysis and a large number of other methods. When a band of the target nucleic acid is hardly distinguishable because of many nonspecific bands, the band of the target nucleic acid can be confirmed by Southern blotting with probes for the specific nucleic acid. From the viewpoint of rapidly detecting the target nucleic acid, the method of detecting the target nucleic acid is particularly preferably the real-time detection method of detection with a probe using a fluorescent label and the method of detection by the turbidity of a byproduct generated upon DNA synthesis.

The treatment solution can be used widely in clinical examination for judging the presence or absence of diseases by the nucleic acid amplification method. Such diseases include, for example, infections, gene-related diseases, and cancers.

Cancer cells leave from a primary focus, and spread via blood stream or the lymphatic system to the whole body. In the operation for cancer, the focus should be removed as accurately as possible, so it is required that its metastasis is accurately detected, and suitable treatment is conducted depending on the metastasis. Accordingly, the diagnosis of metastasis of cancer into the lymph node during the operation has a very important meaning. In breast cancer, for example, the area of the lymph node to be excised in the operation is desirably as small as possible for improving of QOL (quality of life). In esophagus cancer, abdominal operation, breast opening or cervical incision should be selected depending on the site of the cancer spreading in the lymph node. In prostate cancer, whether the operation is to be continued or suspended, whether excision is to be continued and whether hormone therapy is to be conducted should be determined where there is lymph node metastasis. In stomach cancer, the area of the lymph node to be excised and the type of operation are changed depending on the presence or absence of the metastasis of the cancer into the lymph node. In stomach cancer, the presence or absence of the metastasis of the cancer into the lymph node becomes a guideline for the plan of treatment after operation, for example a guideline for selecting whether for example an anticancer drug is to be administered and whether radiotherapy is to be conducted. In this case, if the cancer metastasis can be rapidly diagnosed by using a biological sample collected during operation, the area of the lymph node to be excised, the type of operation to be conducted, and supplementary therapy to be conducted can be determined in operation even for a short time, thus enabling the patient to receive the best treatment. Further, the burden on the patient during operation can be reduced.

When the above-described treatment solution is used, a sample solution for nucleic acid amplification reaction can be rapidly prepared from a biological sample without extracting or purifying a nucleic acid. Accordingly, the treatment solution can be used effectively particularly in cancer metastasis diagnosis that should be completed rapidly by using the nucleic acid amplification method during operation.

The nucleic acid serving as an indicator of cancer includes nucleic acids of cytokeratins such as cytokeratin 18, cytokeratin 19 and cytokeratin 20 and tumor markers such as CEA (carcinoembryonic antigen), PSA (prostate-specific antigen) and CA-15-3 (carbohydrate antigen 15-3).

Example 1

In this example, the effect of DMSO contained in the treatment solution for preparing the sample solution was examined. In this example, the DMSO-containing treatment solution was used to prepare a sample solution for nucleic acid amplification reaction from a biological sample, and the prepared sample solution and a reagent for nucleic acid amplification reaction were used to carry out RT-LAMP.

As the biological sample, commercial cultured cells Molt-4 cells were used. Molt-4 cells are human-derived subcultured tumor cells of acute lymphoblastic leukemia.

As the treatment solution, 4 treatment solutions having different DMSO concentrations of 0% (v/v), 5% (v/v), 10% (v/v) and 20% (v/v), respectively, were used. The composition of the treatment solutions is shown below. The treatment solution contains a surfactant Brij35 (manufactured by Sigma Aldrich Japan) that is polyoxyethylene (23) lauryl ether. As a deforming agent, KS-538 manufactured by Shin-Etsu Chemical Co., Ltd is contained in the treatment solution.

Reagent Composition (Treatment Solution for Preparing the Sample Solution)

| | |
|---|---|
| Glycine buffer (pH 3.0) | 200 mM |
| DMSO | 0-20% (v/v) |
| Brij35 | 5% (v/v) |
| KS-538 | 0.05% (v/v) |

Nucleic acid amplification by RT-LAMP was carried out wherein β-actin RNA was used as the target nucleic acid. β-Actin is expressed at a definite level in every cell.

As the reagent for nucleic acid amplification reaction, a reaction solution, an enzyme solution and a primer reagent containing six primers set forth in SEQ ID NOS: 1 to 6 were used. The composition of each reagent is shown below.

Reagent Composition (Reaction Solution)

| | |
|---|---|
| 750 mM Tris buffer solution (pH 8.0) | 1.00 μL |
| 10 × Thermopol buffer solution (manufactured by New England Bio Lab) | 2.50 μL |
| 10 mM dNTPs | 2.00 μL |
| 100 mM MgSO$_4$ | 0.75 μL |
| 100 mM dithiothreitol | 1.25 μL |
| 2% Tergitol (manufactured by Sigma Aldrich Japan) | 2.50 μL |
| H$_2$O | 3.97 μL |
| Total amount | 13.97 μL |

Reagent Composition (Enzyme Reagent)

| | |
|---|---|
| 10 U/μL AMV reverse transcriptase (manufactured by Promega) | 0.14 μL |
| 8 U/μL Bst DNA polymerase (manufactured by New England Bio Lab) | 2.27 μL |
| RNase inhibitor (manufactured by Promega) | 0.63 μL |
| Total amount | 3.04 μL |

Reagent Composition (Primer Reagent)

| | |
|---|---|
| 80 pmol/μL forward inner primer (SEQ ID NO: 1) | 1.00 μL |
| 80 pmol/μL reverse inner primer (SEQ ID NO: 2) | 1.00 μL |
| 5 pmol/μL forward outer primer (SEQ ID NO: 3) | 1.00 μL |
| 5 pmol/μL reverse outer primer (SEQ ID NO: 4) | 1.00 μL |
| 60 pmol/μL forward loop primer (SEQ ID NO: 5) | 1.00 μL |
| 60 pmol/μL reverse loop primer (SEQ ID NO: 6) | 1.00 μL |
| Total amount | 6.00 μL |

(1) Preparation of a Sample Solution for Nucleic Acid Amplification Reaction 4 mL of the treatment solution was added to 300 mg Molt-4 cells, and the cells were disrupted and homogenized at 25,000 rpm for 90 seconds with a homogenizer manufactured by Microtec Nition. Then, the homogenized solution was centrifuged (10,000×g, 1 minute) to give a supernatant. The resulting supernatant was used as a 1-fold-dilution sample solution. Further, the 1-fold-dilution sample solution was diluted 2-, 4-, 8-, 10- and 16-fold with the treatment solution, to prepare sample solutions different in the degree of dilution.

(2) Amplification of Nucleic Acid by RT-LAMP

Nucleic acid amplification by RT-LAMP was conducted wherein the target nucleic acid was β-actin RNA. First, 13.97 μL of the reaction solution, 3.04 μL of the enzyme reagent and 6.00 μL of the primer reagent were mixed with one another to prepare a reagent mixture. 23 μL of the reagent mixture was mixed with 2 μL of each sample solution prepared in (1), and then reacted at 65° C. for 30 minutes. In detection of the amplified nucleic acid, a Loopamp real-time turbidity measuring instrument (LA-200) manufactured by Teramecs was used. The nucleic acid amplification reaction can be monitored in real time with this instrument by conducting nucleic acid amplification reaction at a predetermined temperature and simultaneously detecting the turbidity of magnesium pyrophosphate formed as an amplification byproduct. In this example, the absorbance was measured at a temperature set at 65° C. for 30 minutes after the sample solution was mixed with the reagent for nucleic acid amplification reaction.

In FIG. 1, the time having elapsed until the absorbance of each sample solution reached 0.1 is shown in bar graph. The time (min) having elapsed until the absorbance (Abs 650 nm) reached 0.1 is shown on the ordinate. The black triangle above the bar graph indicates that the absorbance did not reach 0.1 within the reaction time (30 minutes). The degree of dilution is shown on the abscissa. The following treatment solutions are used in the bar graph from the left to right: the treatment solution at a DMSO concentration of 0%, the treatment solution at a DMSO concentration of 5%, the treatment solution at a DMSO concentration of 10%, and the treatment solution at a DMSO concentration of 20%.

In the samples diluted at relatively low degrees of dilution (diluted 1-, 2- and 4-fold respectively) in FIG. 1, the samples using the treatment solution not containing DMSO (that is, at the DMSO concentration of 0%) showed a longer time having elapsed until the absorbance reached 0.1 than the samples using the treatment solutions containing DMSO (that is, at the concentrations of DMSO of 5%, 10% and 20%, respectively). Herein, the content of an inhibitor in the sample solution is higher as the degree of dilution is lower. From the foregoing, it was found that the influence of an inhibitor contained in the sample solution is reduced by adding DMSO to the treatment solution.

When the times having elapsed until the absorbance reached 0.1 in the samples containing DMSO at the concentrations of 5%, 10% and 20% respectively are compared, the samples containing DMSO at the concentration of 20% and diluted at a lower degree of dilution show a most significant decrease in the time. Even in the sample diluted at 1-fold, the time having elapsed until the absorbance reaches 0.1 is as very short as about 22 minutes. From this result, it was found that when the concentration of DMSO is 20%, the influence of an inhibitor in the sample solution can be more effectively reduced.

Among the sample solutions diluted at relatively high degrees of dilution (diluted 8-, 10- and 16-fold respectively) in FIG. 1, the sample solutions even using the treatment solution not containing DMSO allow the time having elapsed until the absorbance reached 0.1 to be reduced to the same degree as attained by the DMSO-containing sample solutions. This is presumably because by dilution of the sample solution at a high degree of dilution, the concentration of an inhibitor contained in the sample solution is also reduced, thus reducing the influence of the inhibitor.

Example 2

RT-LAMP was carried out in this example wherein various kinds of tissues were used as the biological sample, and the DMSO-containing treatment solution for preparing the sample solution was used.

Nine kinds of tissues (lymph node, ovary, kidney, lung, liver, heart, spleen, stomach and colon) excised from one mouse were used as the biological sample.

As the treatment solution, a buffer solution having the following composition containing 20% (v/v) DMSO was used.

Reagent Composition (Treatment Solution for Preparing a Sample Solution)

| | |
|---|---|
| Glycine buffer solution (pH 3.0) | 200 mM |
| DMSO | 20% (v/v) |
| Brij35 | 5% (v/v) |
| KS-538 | 0.05% (v/v) |

Nucleic acid amplification by RT-LAMP was carried out wherein the target nucleic acid was RNA of glyceraldehyde-3-phosphate dehydrogenase (GAPDH). GAPDH is expressed at a definite amount in every cell.

As the reagent for nucleic acid amplification reaction, the reaction solution used in Example 1, the enzyme solution used in Example 1, and a primer reagent containing six primers set forth in SEQ ID NOS: 7 to 12 were used.

Reagent Composition (Primer Solution)

| | |
|---|---|
| 80 pmol/μL forward inner primer (SEQ ID NO: 7) | 1.00 μL |
| 80 pmol/μL reverse inner primer (SEQ ID NO: 8) | 1.00 μL |
| 5 pmol/μL forward outer primer (SEQ ID NO: 9) | 1.00 μL |
| 5 pmol/μL reverse outer primer (SEQ ID NO: 10) | 1.00 μL |
| 60 pmol/μL forward loop primer (SEQ ID NO: 11) | 1.00 μL |
| 60 pmol/μL reverse loop primer (SEQ ID NO: 12) | 1.00 μL |
| Total amount | 6.00 μL |

(1) Preparation of a Sample Solution for Nucleic Acid Amplification Reaction 4 mL of the treatment solution was added to 300 mg of each kind of tissue, and the cells were disrupted and homogenized at 25,000 rpm for 90 seconds with a homogenizer manufactured by Microtec Nition. Then, the homogenized solution was centrifuged (10,000×g, 1 minute), and the resulting supernatants were diluted respectively 10-fold with the treatment solution, and these were used as the sample solutions.

(2) Amplification of Nucleic Acid by RT-LAMP

Nucleic acid amplification by RT-LAMP was conducted wherein the target nucleic acid was RNA of glyceraldehyde-3-phosphate dehydrogenase (GAPDH). First, 13.97 μL of the reaction solution, 3.04 μL of the enzyme reagent and 6.00 μL of the primer reagent were mixed with one another to prepare a reagent mixture. 23 μL of the reagent mixture was mixed with 2 μL of each sample solution prepared in (1), and then reacted at 65° C. for 30 minutes. In detection of the amplified nucleic acid, a Loopamp real-time turbidity measuring instrument (LA-200) manufactured by Teramecs was used. In this example, the absorbance was measured at a temperature set at 65° C. for 30 minutes after the sample solution was mixed with the reagent for nucleic acid amplification reaction. A sample using rodent total RNA (manufactured by Applied Biosystems) in place of the sample solution was used as a positive control, and a sample using the treatment solution in place of the sample solution was used as a negative control.

Each of FIGS. 2 to 10 is a graph showing the amplification of the GAPDH cDNA in each kind of tissue. In any graphs, the absorbance (Abs 650 nm) is shown on the ordinate and the time (min) on the abscissa. The results are shown in the graphs wherein the following tissues were used as the biological sample: the lymph node in FIG. 2, the ovary in FIG. 3, the kidney in FIG. 4, the lung in FIG. 5, the liver in FIG. 6, the heart in FIG. 7, the spleen in FIG. 8, the stomach in FIG. 9, and the colon in FIG. 10. In each graph, the graph of black-circles is a graph of each kind of tissue, the graph of while circles is a graph of the positive control, and the graph of black triangles is a graph of the negative control.

In FIGS. 2 to 10, the kick-off time of cDNA amplification and the amount of the amplified cDNA where the tissues had been used as the biological sample were similar to those of the positive control. The positive control does not contain any inhibitor. From this result, it was found that the treatment solution can be used for any tissues to reduce the influence of an inhibitor and amplify the target nucleic acid.

Example 3

In this example, a sample solution for nucleic acid amplification reaction was prepared from a biological sample by using the treatment solution (containing 20% (v/v) DMSO) for preparing a sample solution, and the prepared sample solution and a commercial reagent were used to carry out RT-PCR.

As the biological sample, human lymph nodes (A), (B), (C), (D) and (E) wherein cancer metastasis was clinically recognized were used as the biological sample. As the negative control, normal human lymph nodes (F), (G) and (H) were used.

As the treatment solution, the same treatment solution as in Example 2 was used.

Nucleic acid amplification by RT-PCR was conducted wherein the target nucleic acid was cytokeratin 19 (CK19) RNA. It is known that CK19 is expressed in epithelial cells and also expressed in tissues such as lymph node where cancer metastasis is recognized, and also that there is a difference in the expression level thereof between normal tissues and cancer tissues. In this example, 3 primers set forth in SEQ ID NOS: 13 to 15 were used.

RT-PCR was carried out using TaqMan One-step RT-PCR Master Mix Reagents manufactured by Applied Biosystems and Real-time Quantification PCR Unit (ABI PRISMR 7700) manufactured by Applied Biosystems. TaqMan One-step RT-PCR Master Mix Reagents are a reagent kit for RT-PCR, consisting of 2×Master Mix and 40×RNase Inhibitor Mix. The amplified nucleic acid can be quantified with ABI PRISMR 7700 by conducting the nucleic acid amplification reaction at a predetermined temperature for a predetermined time and then detecting fluorescence density increased depending on the amplification of the nucleic acid.

(1) Preparation of Sample Solutions for Nucleic Acid Amplification Reaction 4 mL of the treatment solution was added to 300 mg of each of biological samples (A) to (H), and the cells were disrupted and homogenized at 25,000 rpm for 90 seconds with a homogenizer manufactured by Microtec Nition. Then, the homogenized solutions were centrifuged (10,000×g, 1 minute), and the resulting supernatants were diluted 10-fold with the treatment solution and used as crude mRNA sample solutions (A) to (H), respectively. Using RNeasy Mini Kit manufactured by QIAGEN, mRNAs were purified from the above supernatants and used as purified to give mRNA sample solutions (A) to (H), respectively. The necessary time from purification of mRNA from the supernatant to preparation of the purified mRNA sample solution is approximately 60 minutes.

(2) Amplification of Nucleic Acid by RT-PCR

In this example, RT-PCR was conducted wherein the crude mRNA sample solutions (A) to (H) and the purified mRNA sample solutions (A) to (H) prepared in (1) were used respectively as the sample solution for nucleic acid amplification reaction. First, a reaction solution containing Master Mix, RNase Inhibitor Mix and the 3 primers was prepared, and the reaction solution thus prepared was mixed with the sample solution in order to carry out RT-PCR. RT-PCR consisted of 40 cycles each involving reverse transcription reaction at 48° C. for 30 minutes and keeping the mixture at 95° C. for 10 minutes, then at 95° C. for 15 seconds and at 60° C. for 1 minute. The reaction solution containing Master Mix, RNase Inhibitor Mix and the 3 primers was mixed with the sample solution and regulated such that the final composition became 1×Mater Mix, 1×RNase Inhibitor Mix, 300 nM forward primer (SEQ ID NO:13), 300 nM reverse primer (SEQ ID NO:14) and 200 nM TaqMan Probe (SEQ ID NO:15).

TABLE 1

|  |  | Amount of cDNA (copy/reaction) |
|---|---|---|
| Crude mRNA sample solutions | (A) | $0.50 \times 10^5$ |
|  | (B) | $1.20 \times 10^6$ |
|  | (C) | $0.14 \times 10^5$ |
|  | (D) | $0.14 \times 10^6$ |
|  | (E) | $0.83 \times 10^4$ |
|  | (F) | ND |
|  | (G) | ND |
|  | (H) | ND |
| Purified mRNA sample solutions | (A) | $0.83 \times 10^5$ |
|  | (B) | $0.46 \times 10^6$ |
|  | (C) | $0.11 \times 10^5$ |
|  | (D) | $0.16 \times 10^6$ |
|  | (E) | $0.11 \times 10^4$ |
|  | (F) | ND |
|  | (G) | ND |
|  | (H) | ND |

Table 1 shows the amount of cDNA (copies/reaction) of CK19 amplified by amplification reaction in each sample. The amount of cDNA (copies/reaction) in the table indicates the copy number of CK19 cDNA contained in the mixture after the amplification reaction was finished. In the table, ND refers to a sample wherein the amount of cDNA is less than $10^2$ (copies/reaction), and when the amount of cDNA is in this range, the target nucleic acid is not considered to be amplified.

When the amount of CK19 cDNA amplified by RT-PCR using the crude mRNA sample solution (A) was compared with that using the purified mRNA sample solution (A), the two are very similar to each other. This also applies to the cases of (B) to (E), similarly to the case of (A), wherein when the amount of CK19 cDNA amplified using the crude mRNA sample solution is compared with that using the purified mRNA sample solution, the two are very similar to each other. From these results, it was found that even if the crude mRNA sample solution is used as the sample solution, the amplification product can be obtained in a similar amount to that using the purified mRNA sample solution. In any sample solutions (F) to (H) used as the negative control, no amplification of CK19 cDNA was confirmed.

Example 4

Using a surfactant-containing treatment solution, a sample solution for nucleic acid amplification reaction was prepared in this example from a biological sample, and the amount of RNA contained in the prepared sample solution was measured.

Lymph nodes collected from 4 mice (MRL mice) of the same strain were used respectively as the biological sample. As the treatment solution, treatment solutions (I) to (IV) containing DMSO and a surfactant were used. The composition for the treatment solutions is shown below. The respective treatment solutions are different in the type or concentration of the surfactant contained: that is, the treatment solution (I) contains 1% (v/v) Nonidet P-40 that is polyoxyethylene (9) isooctyl phenyl ether; the treatment solution (II) contains 1.5% (v/v) Brij35 that is polyoxyethylene (23) lauryl ether; the treatment solution (III) contains 3% (v/v) Brij35; the treatment solution (IV) contains 5% (v/v) Brij35.

Reagent Composition (Treatment Solution for Preparing a Sample Solution)

| Glycine buffer solution (pH 3.0) | 200 mM |
|---|---|
| DMSO | 20% (v/v) |
| Surfactant | 1-5% (v/v) |
| KS-538 | 0.05% (v/v) |

(1) Preparation of Sample Solutions for Nucleic Acid Amplification Reaction

The treatment solution (I), (II), (III) or (IV) was added to each mouse lymph node, and the cells were disrupted and homogenized at 25,000 rpm for 90 seconds with a homogenizer manufactured by Microtec Nition. Then, each of the homogenized solutions was centrifuged (10,000×g, 1 minute), and the resulting supernatant was used as a sample solution for nucleic acid amplification reaction. In this example, each sample solution was prepared so as to contain about 1 μL of the treatment solution per 0.075 mg of the biological sample.

(2) Extraction of RNA

RNA contained in the sample solution for nucleic acid amplification reaction obtained in (1) was extracted using RNeasy Mini Kit manufactured by QIAGEN.

(3) Quantification of the RNA

The RNA extract obtained in the method described above was diluted 10-fold with the treatment solution, and the RNA was quantified by measuring the absorbance (Abs 280 nm) of the diluted sample. The results are shown in Table 2.

TABLE 2

|  | Lymph nodes (mg)/ treatment solution (μL) | Amount of RNA (μg/mL) |
|---|---|---|
| (I) | 61 mg/813 μL | 71 μg/mL |
| (II) | 59 mg/787 μL | 122 μg/mL |
| (III) | 75 mg/1000 μL | 97 μg/mL |
| (IV) | 67 mg/893 μL | 115 μg/mL |

Table 2 shows the amount of RNA (μg/mL) in each of the finally obtained sample solutions where each lymph node (mg) was mixed with each treatment solution (μL). (I), (II), (III) and (IV) in the table refer to the cases where the treatment solutions (I), (II), (III) and (IV) were used as the treatment solution, respectively.

Table 1 revealed that when the treatment solutions (I), (II), (III) and (IV) were used, 71 (μg/mL), 122 (μg/mL), 97 (μg/mL) and 115 (μg/mL) RNA were contained respectively, indicating that a sufficient amount of RNA for nucleic acid amplification reaction was contained.

What is claimed is:

1. A method for amplifying a target nucleic acid, without purifying nucleic acid, contained in a tissue derived from a living body, comprising the steps of:
   preparing a first sample solution without purifying nucleic acid by homogenizing a tissue derived from a living body in a treatment solution containing dimethyl sulfoxide, a surfactant and water, the first sample solution containing nucleic acid which is transferred from the tissue;
   preparing a second sample solution without purifying nucleic acid by mixing the first sample solution, deoxyribonucleotide triphosphates, a DNA polymerase and a primer which is complementary to the target nucleic acid; and
   amplifying the target nucleic acid contained in the second sample solution prepared without purifying nucleic acid;
   wherein the pH of the treatment solution is 2.5 to 5.0, and the concentration of dimethyl sulfoxide contained in the treatment solution for reducing the influence of an inhibitor during the target nucleic acid amplification is 5 to 30% (v/v).

2. The method according to claim 1, wherein the concentration of dimethyl sulfoxide contained in the treatment solution is 10 to 25% (v/v).

3. The method according to claim 1, wherein the surfactant is a nonionic surfactant.

4. The method according to claim 3, wherein the nonionic surfactant is a polyoxyethylene-based nonionic surfactant.

5. The method according to claim 1, wherein the amplifying step is carried out by PCR (polymerase chain reaction) or LAMP (loop mediated isothermal amplification of DNA).

6. The method according to claim 1, wherein the second sample solution preparing step is performed by mixing the first sample solution, deoxyribonucleotide triphosphates, an RNA reverse transcriptase, a DNA polymerase and a primer which is complementary to the target nucleic acid.

7. The method according to claim 6, wherein the amplifying step is carried out by RT-PCR (reverse transcriptase-polymerase chain reaction) or RT-LAMP (reverse transcriptase-loop mediated isothermal amplification of DNA).

8. The method according to claim 1, wherein the first sample solution preparing step is performed by homogenizing the tissue in the treatment solution and removing solid materials in the solution rendered homogenous.

9. The method according to claim 8, wherein the solid materials are removed by filtration or centrifugation.

10. The method according to claim 1, wherein the tissue is a lymph node derived from a patient.

11. A method for amplifying a target nucleic acid, without purifying nucleic acid, contained in a tissue derived from a living body, comprising the steps of:
    preparing a first sample solution without purifying nucleic acid by homogenizing a tissue derived from a living body in a treatment solution containing dimethyl sulfoxide, a surfactant and water and by removing solid materials in the solution rendered homogenous, the first sample solution containing nucleic acid which is transferred from the tissue;
    preparing a second sample solution without purifying nucleic acid by mixing the first sample solution, deoxyribonucleotide triphosphates, a DNA polymerase and a primer which is complementary to the target nucleic acid; and
    amplifying the target nucleic acid contained in the second sample solution prepared without purifying nucleic acid;
    wherein the pH of the treatment solution is 2.5 to 5.0, and the concentration of dimethyl sulfoxide contained in the treatment solution for reducing the influence of an inhibitor during the target nucleic acid amplification is 5 to 30% (v/v).

* * * * *